(12) United States Patent
Bowles, Jr.

(10) Patent No.: US 11,224,216 B2
(45) Date of Patent: Jan. 18, 2022

(54) CLOSURE APPARATUS

(71) Applicant: Aaron Victor Bowles, Jr., San Antonio, TX (US)

(72) Inventor: Aaron Victor Bowles, Jr., San Antonio, TX (US)

( * ) Notice: Subject to any disclaimer, the term of this patent is extended or adjusted under 35 U.S.C. 154(b) by 461 days.

(21) Appl. No.: 16/240,700

(22) Filed: Jan. 4, 2019

(65) Prior Publication Data

US 2019/0208767 A1    Jul. 11, 2019

Related U.S. Application Data (60) Provisional application No. 62/614,327, filed on Jan. 5, 2018.

(51) Int. Cl.
| | | |
|---|---|---|
| *A01N 1/00* | (2006.01) | |
| *A61F 5/37* | (2006.01) | |
| *A61G 17/00* | (2006.01) | |
| *A61B 16/00* | (2006.01) | |

(52) U.S. Cl.
CPC ............... *A01N 1/00* (2013.01); *A61B 16/00* (2013.01); *A61F 5/3707* (2013.01); *A61G 17/00* (2013.01)

(58) Field of Classification Search
CPC .... A61F 5/3707; A61F 5/05808; A61F 5/055; A01N 1/00; A61G 17/044; A61G 13/122; A61G 13/121; A61G 13/1215; Y10S 602/902; Y10S 128/19; Y10S 128/23
See application file for complete search history.

(56) References Cited

U.S. PATENT DOCUMENTS

| | | | | | |
|---|---|---|---|---|---|
| 197,243 | A | * | 11/1877 | Boylston | A61G 17/044 27/25.1 |
| 306,685 | A | * | 10/1884 | Hecox | A01N 1/00 27/25.1 |
| 506,886 | A | * | 10/1893 | Sexton | A01N 1/00 27/25.1 |
| 771,982 | A | * | 10/1904 | Hiser | A61G 17/044 27/25.1 |
| 1,299,670 | A | * | 4/1919 | Brady | A01N 1/00 27/25.1 |
| 4,700,697 | A | * | 10/1987 | Mundell | A61F 5/055 128/DIG. 23 |
| 4,765,317 | A | * | 8/1988 | Eastman | A61F 5/055 602/32 |
| 5,289,829 | A | * | 3/1994 | Roehrig | A61F 5/56 128/848 |

(Continued)

OTHER PUBLICATIONS

Jones, Oliver; The Anterior Triangle of the Neck; Nov. 19, 2020; teachmeanatomy.info/neck/areas/anterior-triangle (Year: 2020).*

*Primary Examiner* — Catharine L Anderson
*Assistant Examiner* — Arjuna P Chatrathi
(74) *Attorney, Agent, or Firm* — Shah IP Law, PLLC (57) ABSTRACT

An apparatus for keeping a deceased person's mouth closed is disclosed herein. The apparatus ensures that the deceased person's mouth does not open during a period of muscle relaxation that immediately follow death, and ensures that the deceased mouth is not open during rigor mortis, which makes it more difficult to close the deceased open mouth later. The apparatus is comprised of various modular and swappable elements to ensure universal fit, as well as anti-slippage elements that ensure that the apparatus does not slip off a person's body when in use.

17 Claims, 2 Drawing Sheets

(56) References Cited

U.S. PATENT DOCUMENTS

| | | | | |
|---|---|---|---|---|
| 6,171,314 B1* | 1/2001 | Rotramel | ............ | A61F 5/05891 602/18 |
| 6,725,511 B1* | 4/2004 | Rødseth | ................... | A01N 1/00 27/25.1 |
| 7,789,843 B2* | 9/2010 | Ray | ........................ | A61F 5/055 602/18 |
| 7,850,630 B1* | 12/2010 | Vu | ...................... | A61F 5/05883 602/17 |
| 8,382,692 B1* | 2/2013 | Chao | ........................ | A61F 5/01 602/18 |
| 2008/0041374 A1* | 2/2008 | Reddick | ................. | A61G 13/12 128/200.26 |
| 2009/0095309 A1* | 4/2009 | Derrick | ................. | A61F 5/3707 128/870 |
| 2013/0333708 A1* | 12/2013 | Hassan | .................. | A61F 5/055 128/848 |
| 2015/0305913 A1* | 10/2015 | Calegory | ................ | A61F 5/055 602/17 |

\* cited by examiner

CLOSURE APPARATUS

CROSS-REFERENCE TO RELATED APPLICATIONS

This application claims priority to U.S. Provisional Patent Application Ser. No. 62/614,327, filed Jan. 5, 2018, entitled "Jaw Securing System and Method of Use." The entire content of the application is incorporated herein by reference.

BACKGROUND

Field of the Art

This invention relates generally to an apparatus for use on a human body. More particularly, the present invention relates to an apparatus that helps keep a human mouth in a closed position.

Discussion of the State of the Art

The human body typically goes through several changes after a person passes away. Generally, immediately following death, the muscles in the human body tend to relax. This causes limbs and other body parts, such as the mouth and eyes to become open. More specifically, as the muscles around the jaw relax, the mouth tends to become open. This is generally considered an undesirable final state because saliva and other fluids in the mouth release and drip down the person's face. Moreover, many consider an open mouth to be an unattractive final state, especially if the deceased will be viewed in an open casket configuration. Thus, it is often desirable to ensure that the deceased mouth is closed after he or she passes away.

The difficult in keeping the deceased mouth closed is often compounded by the second stage of decomposition that a human body undergoes after death. Generally, following the above described period of muscle relaxation, the body goes through rigor mortis, which is characterized by the stiffening of the muscles and joints. It becomes much more difficult to close the deceased's mouth if it is left open when rigor mortis sets in.

To overcome these challenges, hospice workers often try to close the mouths of the recently deceased with tape, or by placing rolled up towels under the deceased person's chin. However, these solutions are ineffective. Tape, for example, often falls off. Rolled up towels rarely stay in place, and often sag under the weight of the deceased person's jaw. Moreover, it is generally undesirable to use ad-hoc solutions like these because it makes hospice workers uncomfortable. Finally, current ad-hoc solutions are unattractive and tend not to alleviate the trauma experienced by loved ones when they see deceased with tape on their mouth or with towels wider their chins.

Some have proposed devices or apparatuses that sit on the deceased's neck to keep deceased's mouth closed. But these solutions are not adjustable. Indeed, these devices are often made with as few moving parts as possible to preserve their structural integrity and prevent bucking or bending wider the weight of a person's chin. Because of these limitations, these devices do not fit a variety of different neck sizes and neck lengths. As a result, these devices have limited commercial adoption because hospice workers are forced to keep a large number of these devices on hand in a number of variety of sizes, which ultimately drive up the cost associated with using such devices. Moreover, these solutions are undesirable because hospice workers, who are often overwhelmed with a number of other responsibilities, are loathe to keep trying a variety of different sizes to find one that fits.

SUMMARY

The inventor has conceived and reduced to practice an apparatus for keeping a person's mouth closed when the apparatus is placed on a person. A feature of the present invention is that is modular, flexible, and adjustable such that it can be used on persons with a variety of different neck sizes, neck lengths, and weights. Moreover, the inventive apparatus is comprised of features or elements to ensure that the apparatus does not fall-off or move around. For example, inventive apparatus ensures that the person's mouth does not open inadvertently, by, for example, ensuring that the apparatus does not move around when the apparatus is placed on a person.

Generally, the inventive apparatus is comprised of a top platform, a bottom platform, and one or more tension rods. The top platform securely affixes to an area under a person's chin. The bottom platform securely affixes to an area over a person's collarbone. The one or more tension rods attach to the top platform on one end, and attach to the bottom platform on the other end. The one or more tension rods bow out when connected to the top platform and the bottom platform, and apply pressure to both platform to ensure that the person's mouth remains closed. In one embodiment of the invention, the one or more tension rods are easily removable, and may be swapped out with tension rods that are longer or shorter to accommodate persons with variety of different neck sizes, neck lengths, and weights. As such, the inventive apparatus is modular, and works universally with a variety of different people.

Moreover, the inventive apparatus overcomes many of the dislodgment issues that are typically associated with trying to keep a person's mouth closed with an external apparatus. For example, the top platform is shaped to fit in the soft tissue area between a person's mandibular bone. This feature ensures that the apparatus does not move around under the user's chin and ensure that the person's mouth does not become open inadvertently when pressure is applied to the top platform via the one or more tension rods. In one embodiment of the invention, the bottom platform is comprised of anti-slippage elements such as an extension element that securely affixes to a person's jugular notch. In one embodiment of the invention, the bottom platform is comprised of anti-slippage elements such as one or more channels that securely affix to a person's one or more clavicular bone.

Although the inventive apparatus is described herein as being used on a deceased person, the inventive apparatus may be used in a number of different settings. For example, the inventive apparatus may be used in medical emergency situations where it is desirable to keep a person's mouth closed. In some instances, the inventive apparatus may be used on terminally ill patients or non-responsive patients and the like, without departing from the scope of the invention.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

The inventor has conceived, and reduced to practice, an assistive apparatus for ensuring that a deceased person's mouth remains closed. Specifically, the inventive apparatus is for a flexible and modular apparatus for securely closing the jaw of a deceased person, the apparatus comprising a bottom platform for securely placing the apparatus on the deceased person's collarbone, the bottom platform comprising anti-slippage elements to prevent the apparatus from moving or slipping when the apparatus is placed between the deceased person's chin and collarbone, a top platform for securely placing the apparatus under the deceased person's chin, the top platform comprising a contouring shape to prevent the apparatus from moving when the apparatus is placed between the deceased person's chin and collarbone; and a removable tension rod connecting the bottom platform to the top platform, the removable tension rod being flexible and bendable to support a variety of different neck lengths, and jaw weights while still applying enough pressure on the deceased person's chin to ensure that it remains closed, the tension rod being removable from the top platform and the bottom platform to accommodate longer or shorter tension rods, and the tension rod being pre-curved to ensure that the apparatus does not apply excessive force on the deceased person's clavicle or chin. The apparatus's anti-slippage element on the bottom platform is further comprised of an extension portion that, when placed on the deceased person's collarbone, fits within the deceased person's jugular notch. The apparatus's anti-slippage element on the bottom platform is further comprised of a channel that, when placed on the deceased person's collarbone, fits over the deceased person's clavicle. The apparatus's anti-slippage element on the bottom platform is further comprised on two channels, wherein each channel fits over each clavicle of the deceased person when the apparatus is placed on the deceased person's collarbone. In one embodiment, the apparatus's top platform is designed to fit within the submental triangle and between the mandibular bone of a deceased person. In one embodiment, the apparatus's top platform is circular. In one embodiment, the uppermost surface of the top platform is convex. In one embodiment, the top platform is triangular. In one embodiment, the apparatus's top platform and the bottom platform are each further comprised of a cavity that receives a portion of the tension rod and securely holds the tension rod in place. In one embodiment, the cavities on the top platform and the bottom platform each receive a portion of the tension rod at a particular angle. In one embodiment, the cavity on the top platform receives a portion of the tension rod at an approximately thirty-degree angle, and the cavity on the bottom platform receives a portion of the tension rod at an approximately twenty-degree angle. In one embodiment, the cavities on the top platform and the bottom platform narrow in diameter as they extend inwards into each the top platform and the bottom platform. In one embodiment, the apparatus's tension rod is comprised of a nylon material that flexes under pressure. In one embodiment, the tension rod is comprised of a nylon material that resists flexing beyond a certain value. In one embodiment, the apparatus's tension rod bows out when the apparatus is placed on a deceased person to accommodate the deceased person's trachea. A feature of the present invention comprises additional tension rods that may also connect the bottom platform to the top platform. In one embodiment, the apparatus's top platform and the bottom platform are comprised of textured material that prevents the apparatus from moving when placed on a deceased person. In one embodiment, the tension rod may be removed from the top platform and the bottom platform and be replaced with another tension rod that may be longer or shorter to accommodate necks that are longer or shorter in length.

The invention is described by reference to various elements herein. It should be noted, however, that although the various elements of the inventive apparatus are described separately below, the elements need not necessarily be separate. The various embodiment may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

Overview

Figure 1:
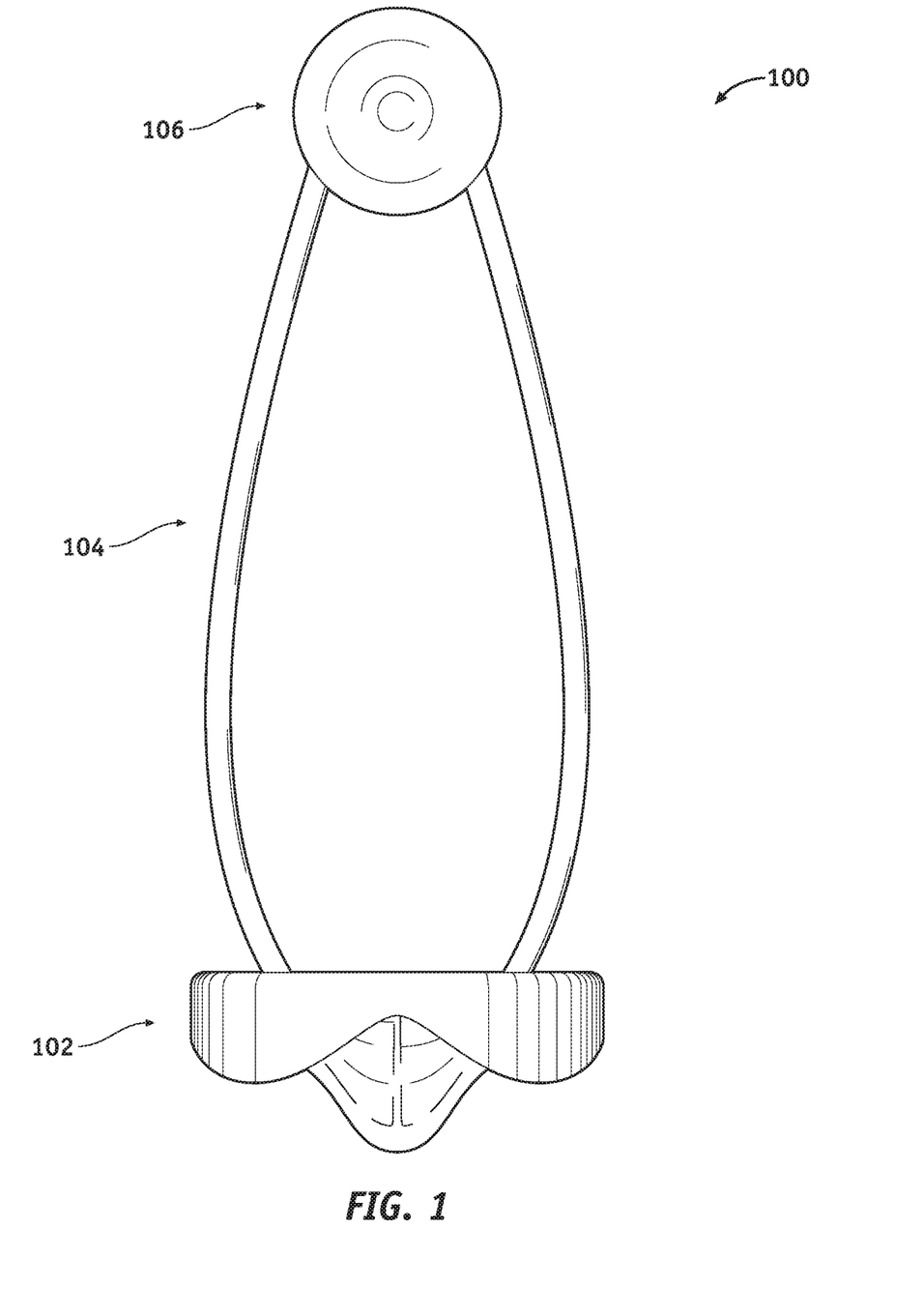
FIG. 1 illustrates, in accordance to one embodiment of the invention, an exemplary inventive apparatus.

Now referring to FIG. 1, which illustrates an exemplary inventive apparatus 100 in accordance with an embodiment of the invention. It is comprised of a top platform 106, a bottom platform 102, and tension rods 104.

The various elements assemble together to form the inventive apparatus 100. The entire apparatus 100 may be placed under a person's chin, and over the person's collarbone. The tension from the tension rods 106 ensure that the person's mouth remains closed while the apparatus is placed on the person.

Top Platform

Figure 3:
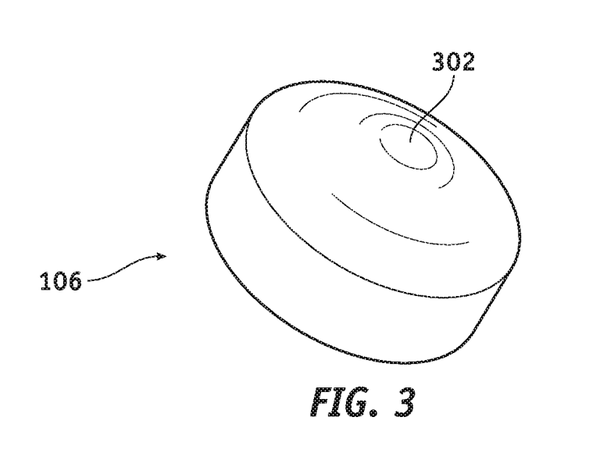
FIG. 3 illustrates, in accordance to one embodiment of the invention, an exemplary top platform of the inventive apparatus.

FIG. 3 illustrates the top platform 106 in accordance to an embodiment of the invention. The top platform 106 affixes to the base of a person's mandible, and helps keep the person's jaw closed when sufficient upward pressure is applied the top platform 106, via, for example, one or more tension rods 104.

In one embodiment of the invention, the top platform 106 is shaped to ensure that it fits at the base of variety of different persons' mandible. Generally, the base of the mandible is comprised of a submandibular triangle, which may be characterized as a soft spot in-between the mandibular base. Thus, in accordance with one embodiment of the invention, the top platform 106 may be shaped to fit within the submandibular triangle. In one exemplary embodiment, the top platform 106 may be circular in shape and designed to fit within the submandibular triangle.

The specific shape and size of the submandibular triangle may vary from person to person. Thus, the top platform 106 may be shaped so that it can fit within a variety of different submandibular triangles. In one embodiment of the invention the top platform 106 may be circular in shape. In such a configuration, the top platform 106 may sit closer to the corner under the chin formed by the mandibular base if a user's mandibular forms a wide base. Conversely, if the user's mandibular base forms a narrow angle, then the top platform 106 may sit further away from the corner under the chin formed by the mandibular base. In other embodiments of the invention, the top platform 106 may be triangular in shape that is similar to the shape formed by the interior portion of the submandibular triangle. However, the shape and size of the top platform 106 is not limited to specific shapes described herein, and a variety of different curvatures and sizes may be used without departing from the scope of the invention, including, but not limited to square, circle, hexagon, octagon, etc.

In one embodiment of the invention, the top surface of the top platform 106 may be contoured for greater stability and security against movement. For example, the top surface of the top platform 106 may comprise a raised portion 302 that extends from the center of top platform 106. The device may slope down or taper down form the raised portion 302 in all direction. This configuration essentially creates a clear point of contact that securely lodges into a particular portion of the submandibular triangle, thereby reducing the likelihood that the top platform 106 may slip out from user the person's neck. The invention is not limited to one raised portion formed over the top surface of the top platform 106. A number of different configurations may be used to improve the amount of friction that may be applied to the submandibular triangle to ensure that the user's face does not fall off the apparatus 100, including, but not limited to, multiple raised portions, angular raised surfaces such as pyramids, etc.

In one embodiment of the invention, the top surface of the top platform 106 may comprise an additional gripping surface material that prevents slippage between the top platform 106 and the base of the persons mandible. For example, the top surface of the top platform 106 may be comprised of a textured surface or an adhesive or the like. The material may be etched onto the top surface, may be applied externally via a coating, or may be impregnated within the top platform 106. The platform itself may optionally have a rough or textured surface so as to increase friction and adherence to the body or surfaces without the need for additional layers or adhesives.

In one embodiment of the invention, the bottom surface of the top platform 106 may be comprised of one or more cavities that each accommodates one or more tension rods 104. The cavities enable the one or more tensions rods 104 to connect to the top platform 106 to the bottom platform 102. In one embodiment of the invention, the cavity is a hollow tunnel with a diameter that is slightly larger than the diameter of one or more tension rods 104. In one embodiment of the invention, the diameter of cavity is tapered such that the opening of the cavity is wider at the surface of the top platform 106 and narrowed within the top platform 106. This feature enables the cavities to grip the one or more tension rods securely. In one embodiment of the invention, the cavities enable the one or more tension rods to attach to the top platform 106 at an approximately thirty-degree angle. In one embodiment of the invention, the top platform 106 may be affixed to the one or more tension rods with other methods or systems with departing from the scope of the invention, including, for example, but not limited to fasteners, adhesive, latches, hinges, welding techniques, or any other method that may be used by a person of ordinary skill in the art.

Bottom Platform

Figure 2A:
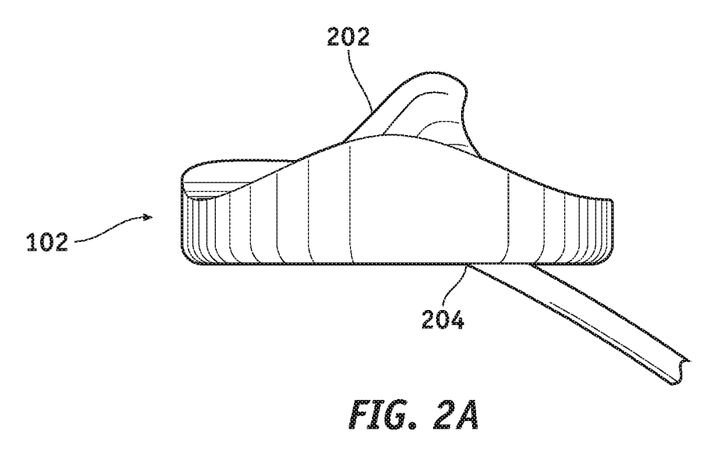
FIG. 2a illustrates, in accordance to one embodiment of the invention, an exemplary bottom platform of the inventive apparatus.
Figure 2B:
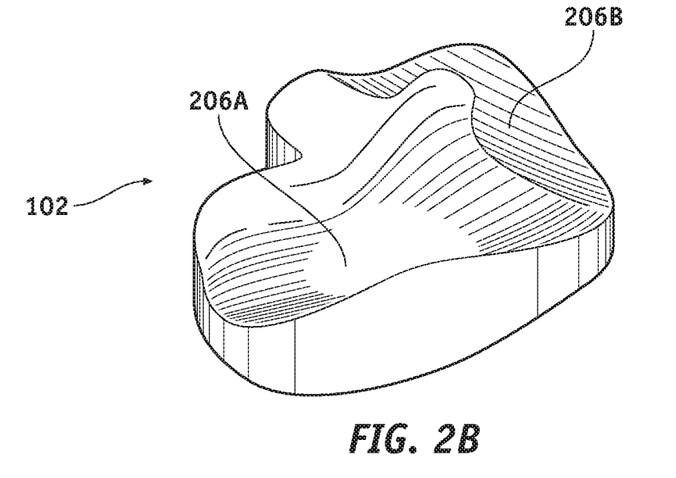
FIG. 2b illustrates, in accordance to one embodiment of the invention, an exemplary bottom platform of the inventive apparatus.

Referring now to FIGS. 2a and 2b, which illustrate the bottom platform 102. The bottom platform 102 operates as the foundation and an anchor for the inventive apparatus 100; it sits under a user's neck and over his or her upper chest and is comprised of features that ensure that the apparatus 100, when used on a person, does not move when or slip from the user's body when pressure is applied via the device to the user's jaw in an effort to keep it closed.

In one embodiment of the invention, the bottom platform 102 may be placed at about a person's sternoclavicular joint or other parts of the upper chest such as the clavicle, sternum, ribs, sternocostal joint. In one embodiment of the invention, a portion of the bottom platform 102 (specifically, a portion of the bottom surface of the bottom platform 102 that contacts the user's upper chest) sits in the jugular notch of the user, and a second portion of the platform's 102 bottom surface sits over the user's one or more clavicle bone.

In one embodiment of the invention, the bottom platform 102 may be shaped like a heart. However, as would be readily apparent to a person of ordinary skill in the art, the bottom platform 102 may have any shape, including a triangle, a circle, a diamond, a hexagon, etc., as long as it conforms to the description here without departing from the scope of the invention.

In one embodiment of the invention, the bottom platform 102 is comprised of one or more anti-slippage elements that ensure that the platform 102 and the apparatus 100 do not slip out when in use. In one embodiment of the invention, the bottom platform 102 is comprised of an extension portion that interacts with the user's sternoclavicular joint to ensure that the apparatus 100 does not slip out when in use.

Referring now to FIG. 2a, it Illustrates the bottom platform 102 in accordance to an embodiment of the invention. It is comprised of an extension portion 202 that extends beyond the bottom surface of the bottom platform 102. The bottom surface of the bottom platform 102 sits on top of a person's upper chest. The extension portion 202, when place over a person's clavicular joint, lodges itself with the person's jugular cavity. As such, the shape and size of the extension portion 202 may vary to accommodate jugular cavities of a variety of different shapes and sizes. In one embodiment of the invention, the extension portion 202 may be designed to be lodged within other cavities in the clavicular joint, including but not limited to the clavicular notch, etc. As would be readily apparent to a person of ordinary skill in the art, the specific shape and size of the extension portion 202 may be modified to fit a variety of different cavities and notches within the clavicular joint.

Referring now to FIG. 2b, it illustrates the bottom platform 102 from a side perspective view, in accordance to an embodiment of the invention. It is comprised of other anti-slippage elements, channel 206a and channel 206b. The two channels may sit on top of the clavicular bone when the bottom platform's 102 bottom surface is placed over a person's clavicular joint. When placed in this manner, the channels 206a and 206b ensure that the bottom surface 102 and the apparatus 100 do not slip from a person's body when the apparatus 100 is in use. In one embodiment of the invention, the channels 206a and 206b may be of a shape and size that accommodates clavicular bones of a large variety of different persons. Generally, the channels 206a and 206b may be semi-cylindrical in shape to conform to the clavicular bone. In one alternative embodiment of the invention, the bottom platform 102 may comprise only one channel 206a or 206b, which may sit on one clavicular bone of a user or a person.

In one embodiment of the invention, the bottom surface of the bottom platform 102 may comprise an additional gripping surface material that prevents slippage between the bottom platform 102 and the user's clavicular joint. For example, the bottom surface of the bottom platform 102 may be comprised of a textured surface or an adhesive or the like. The material may be etched onto the bottom surface, may be applied externally via a coating, or may be impregnated within the bottom platform 102. The platform itself may optionally have a rough or textured surface so as to increase friction and adherence to the body or surfaces without the need for additional layers or adhesives.

Referring again to FIG. 2a, it illustrates the bottom platform 102 with two tension rods 104 extending from the "top" surface of the bottom platform 102. Although not shown in the figures, the top surface of the bottom platform 102 is comprised of one or more cavities that accommodate the one or more tension rods 104. In one embodiment of the invention, the top surface of the bottom platform 102 may be comprised of one or more cavities that each may accommodate one or more tension rods 104. The cavities enable the one or more tensions rods 104 to connect to the bottom platform 102 to the top platform 106. In one embodiment of the invention, the cavity is a hollow tunnel with a diameter that is slightly larger than the diameter of one or more tension rods 104. In one embodiment of the invention, the diameter of cavity is tapered such that the opening of the cavity is wider at the surface of the bottom platform 102 and narrowed as the cavity approaches the center of the bottom platform 102. This feature enables the cavities to grip the one or more tension rods securely. In one embodiment of the invention, the cavities enable the one or more tension rods to attach to the bottom platform 102 at an approximately twenty-degree angle. In one embodiment of the invention, the bottom platform 102 may be affixed to the one or more tension rods with other methods or systems with departing from the scope of the invention, including, for example, but not limited to fasteners, adhesive, latches, hinges, welding techniques, or any other method that may be used by a person of ordinary skill in the art.

Tension Rods

Referring again to FIG. 1, which illustrates tension rods 104 that connect the bottom platform 102 to the top platform 106 in accordance with an exemplary embodiment of the invention. The tension rods, when connected to both platforms 102 and 106, apply pressure, which ultimately is transferred to the user's jaw and cause the mouth to remain closed when the apparatus 100 is in use. Although two tension rods 104 are illustrated in FIG. 1, any number of one or more tension rods 104 may be used without departing from the scope of the invention.

In one embodiment of the invention, the tension rods 104 are pre-bowed such that they may be flex a little when weight is applied to them, but do not snap back against the weight, which may potentially cause the tension rods 104 or the apparatus 100 to cause harm or injury to the user or the person applying the apparatus onto a person. In addition, the tension rods 104, when attached to the top platform 106 and the bottom platform 102 bow in a direction that is away from the user's neck. In one embodiment, the tension rods 104 bow or flex in a direction that is halfway between the wearer's shoulder and a central plane extending directly forward from the center of the wearer's neck. This configuration permits the apparatus 100 to accommodate a variety of different neck size without creating additional obstructions. In one embodiment of the invention, the tension rods 104 may be made of nylon material, but a variety of different materials may be used, as would be readily understood by a person of ordinary skill in the art, without departing from the scope of the invention.

An aspect of the invention is that the tension rods 104 may be replaceable by a user. For example, the tension rods 104 may be made available in a variety of different lengths to accommodate necks of different lengths. Through this feature, the apparatus 100 may be used on a wide number of people without requiring separate devices for each person. In one commercial aspect of the invention, the tension rods 104 may be supplied in a small, medium, or large lengths to accommodate person of a large variety of different neck sizes.

In one embodiment of the invention, the tension rods may comprise an adjustable portion to adjust the length of the tension rods. The adjusting mechanism may be comprised of a plurality of tension rods connected by one or more wires arranged in a left and right assembly positioned on the left and right side respectively of the top platform and bottom platform with a hollow portion between the left and right assembly. The tension rods are preferably made of Delrin™ acetal plastic or other engineering thermoplastic material having a cross-sectional thickness and smoothness with strong resiliency, high modulus of elasticity and strength, and fatigue resistance whereby the rods may be compressed by force and then expand once the force is no longer applied. In further embodiments the tension rods may be made of compressible fiber or rubber material. The tension rods may have an aperture, which is sized to accommodate and secure one or more wires. The wire is preferably made of a bendable metal, plastic, or rubber having a long fatigue and strong life wherein when the wire is bent to a selected angle of form, the wire remains at the selected angle of form, until the wire is once again bent In some non-limiting embodiments the tension rods may be connected by a plurality of wires braided, twisted, or otherwise fastened together.

The metal wires may be surrounded by another material such as a moldable rubber or rubber-like plastic material that is molded in place around the wire or is connected with any other fasteners, adhesive, welding techniques used by those of ordinary skilled in the art. The covering increases longevity of the wire by shielding it from external elements. In further embodiments a single wire may pass through each tension rod on an assembly while in other embodiments separate wires connect adjacent tension rods.

The rods may be compressed by force applied by the user and expanded once the force is released whereby the rods are positioned between the base of the mandible and the sternoclavicular joint keep the mouth of the person from opening. The left and right assembly may have each have an upper tension rod wherein the upper tension rods are cylindrical in shape and fit securely into circular slots of the top platform and a lower tension rod, cylindrical in shape, wherein the lower tension rods fit securely into the circular slots of the bottom platform. In further non-limiting embodiments the tension rods may be spring based apparatuses comprised of a smaller rod and larger rod with a high-tension spring affixed to one end of the smaller rod and placed inside the larger rod where it is affixed to one end of the larger rod. The smaller rod is then pushed into the larger rod, causing the spring to compress. The larger rod may then be fitted with a special gasket or crimped slightly on one end to prevent the smaller rod from leaving the inside of the larger rod completely. Because the spring is compressed, the spring pushes out against one end of the larger rod and one end of the smaller rod, creating tension to push against the top platform to apply pressure upward against a person s mandible to keep the mouth closed.

In further non-limiting embodiments the one or more wires on the left assembly and the right assembly may be affixed to a crossbar connecting the right assembly and left assembly wherein the crossbar functions as a stability component to hold the system together as well as against the person s body. The crossbar may be affixed to the one or more wires with, for example, fasteners, adhesive, welding techniques, or any other method known by those skilled in the art. Those of ordinary skill in the art will appreciate that the steps may be of any order such as the user placing the bottom platform on the sternoclavicular joint on the person before positioning the top platform as well as adjusting the adjusting mechanism before positioning either platform. The device then may be removed by the user adjusting the adjusting mechanism whereby it is no longer connected to two parts of the persons body and may be removed without harming the person. The device may be cleaned by the use of disinfectant wipes or hand washing or any other method applied to similar medical devices known by those skilled in the art.

In some non-limiting embodiments the adjusting mechanism may be a latch mechanism made of a plastic material or any other suitable material such as steel or fiber and is comprised of a push button mechanism operable in relation to a extension body wherein the push button locking device is used to selectively alter the length of the extension body, thereby adjusting the height of the system to accommodate for the varying distances between the bottom of the jaw and a notch, collar bones, or any other part of the upper chest.

In one embodiment the adjusting mechanism may be comprised of a latch mechanism. The extension body is comprised of a left and right segment positioned symmetrically around the vertical axis of the system. Each segment has an outer component and inner component In each segment are aligned holes formed in the outer component and are of a certain distance from one another. In each segment a push button mechanism may be positioned within the inner component so as to protrude through the left and right series of aligned holes formed in the outer component and through a hole formed in the inner component. The push button mechanism is provided with a button whereby the user may use a depressing force to push the button. The button is fixed to a spring clip but any such electrical, hydrologic, pneumatic mechanisms known to those skilled in the art may be used as the push button mechanism. The clip is preferably formed of a resilient metal strip bent over on itself and having a distal side which, when compressed within the inner component, exerts an outward force on the button. This outward force maintains the push button mechanism in an engaged position within the inner component with the buttons extending through the holes in the inner component and the series of aligned holes of the outer component. In some embodiments the ends of the inner component and outer component may be designed to prevent complete displacement of the inner component from the outer component or have a method or system such as a gasket, crimping, or any other known methods or systems to those of ordinary skill in the art to prevent complete displacement of the inner component from the outer component With the latch mechanism in the present invention, the user may adjust the height of the system to accommodate for varying distances between beneath the base of the mandible and the sternoclavicular joint or any other part of the upper chest Engaging the push button mechanism releases the latch mechanisms onto a disengaged position whereby the outer component of the extension body may freely move relative to the inner component in a linear telescopic motion. The upward motion of the outer component relative to the inner component lengthens the extension body of the system whilst a downward motion of the outer component relative to the inner component shortens the extension body. Once the depressing force placed upon the button by the user is terminated, the expansive force of the push button mechanism causes the button to protrude out of the first of the aligned holes with which it comes into alignment, preventing any further movement In further non-limiting embodiments the push button mechanism may only be fixed to one segment whilst the second segment is held in position by the push button mechanism on the first segment In even further embodiments the system may be comprised of only two components including a top platform or bottom platform having the inner component of the extension body built into it and the other platform having the outer component of the extension tube whereby when the button is depressed the push button mechanism releases the latch mechanisms onto a disengaged position whereby the outer component of the extension body may freely move relative to the inner component in a linear telescopic motion. In further embodiments the system may only have one latch system in the middle of the system connecting the top and bottom platform. Those of ordinary skill in the art will appreciate that the latch mechanism may include any number of buttons and holes in various configurations and is not limited to the number depicted in the attached illustrations or described above.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A flexible and modular apparatus for securely closing the jaw of a deceased person, the apparatus comprising:
   a bottom platform for securely placing the apparatus on the deceased person's collarbone, the bottom platform comprising anti-slippage elements to prevent the apparatus from moving or slipping when the apparatus is placed between the deceased person's chin and collarbone;
   a top platform for securely placing the apparatus under the deceased person's chin, the top platform comprising a contouring shape to prevent the apparatus from moving when the apparatus is placed between the deceased person's chin and collarbone;
   a removable tension rod connecting the bottom platform to the top platform, the removable tension rod being flexible and bendable to support a variety of different neck lengths, and jaw weights while still applying enough pressure on the deceased person's chin to ensure that it remains closed, the tension rod being removable from the top platform and the bottom platform to accommodate longer or shorter tension rods, and the tension rod being pre-curved to ensure that the apparatus does not apply excessive force on the deceased person's clavicle or chin; and
   an additional removable tension rod that also connects the bottom platform to the top platform.

2. The apparatus of claim 1, wherein the anti-slippage element of the bottom platform is further comprised of an extension portion that, when placed on the deceased person's collarbone, fits within the deceased person's jugular notch.

3. The apparatus of claim 1, wherein the anti-slippage element of the bottom platform is further comprised of a channel that, when placed on the deceased person's collarbone, fits over the deceased person's clavicle.

4. The apparatus of claim 1, wherein the anti-slippage element of the bottom platform is further comprised of two channels, wherein each channel fits over each clavicle of the deceased person when the apparatus is placed on the deceased person's collarbone.

5. The apparatus of claim 1, wherein the contouring shape of the top platform is designed to fit within the submental triangle and between the mandibular bone of a deceased person.

6. The apparats of claim 5, wherein top platform is circular.

7. The apparatus of claim 5, wherein the uppermost surface of the top platform is convex.

8. The apparatus of claim 1, wherein the top platform and the bottom platform are each further comprised of a cavity that receives a portion of the tension rod and securely holds the tension rod in place.

9. The apparatus of claim 8, wherein the cavities on the top platform and the bottom platform each receive a portion of the tension rod at a particular angle.

10. The apparatus of claim 9, wherein the cavity on the top platform receives a portion of the tension rod at an approximately thirty degree angle.

11. The apparatus of claim 9, wherein the cavity on the bottom platform receives a portion of the tension rod at an approximately twenty degree angle.

12. The apparatus of claim 8, wherein the cavities on the top platform and the bottom platform narrow in diameter as they extend inwards into each the top platform and the bottom platform.

13. The apparatus of claim 1, wherein the tension rod is comprised of a nylon material that flexes under pressure.

14. The apparatus of claim 1, wherein the tension rod is comprised of a nylon material that resists flexing beyond a certain value.

15. The apparatus of claim 1, wherein the tension rod bows out when the apparatus is placed on a deceased person to accommodate the deceased person's trachea.

16. The apparatus of claim 1, wherein the top platform and the bottom platform are comprised of textured material, which prevents the apparatus from moving when placed on a deceased person.

17. The apparatus of claim 1 wherein the tension rod may be removed from the top platform and the bottom platform and be replaced with another tension rod that may be longer or shorter to accommodate necks that are longer or shorter in length.

* * * * *